(12) United States Patent
Richerme et al.

(10) Patent No.: US 9,693,871 B2
(45) Date of Patent: Jul. 4, 2017

(54) VERTEBRAL IMPLANT PROVIDED WITH A SELF-LOCKING AND UNLOCKING MEANS

(71) Applicants: Pierre Dominique Richerme, Praz sur Arly (FR); Stéphane Ramare, Le Chesnay (FR); Christophe Tamburini, Saint Laurent de Mure (FR)

(72) Inventors: Pierre Dominique Richerme, Praz sur Arly (FR); Stéphane Ramare, Le Chesnay (FR); Christophe Tamburini, Saint Laurent de Mure (FR)

(73) Assignee: SPIRITS, Lyons (FR)

( * ) Notice: Subject to any disclaimer, the term of this patent is extended or adjusted under 35 U.S.C. 154(b) by 0 days.

(21) Appl. No.: 14/403,431

(22) PCT Filed: May 24, 2013

(86) PCT No.: PCT/FR2013/051153
§ 371 (c)(1),
(2) Date: Nov. 24, 2014

(87) PCT Pub. No.: WO2013/175147
PCT Pub. Date: Nov. 28, 2013

(65) Prior Publication Data
US 2015/0142115 A1 May 21, 2015

(30) Foreign Application Priority Data
May 25, 2012 (FR) ...................... 12 54831

(51) Int. Cl.
*A61F 2/44* (2006.01)
*A61F 2/30* (2006.01)
*A61B 17/80* (2006.01)

(52) U.S. Cl.
CPC ................ *A61F 2/442* (2013.01); *A61F 2/44* (2013.01); *A61F 2/447* (2013.01);
(Continued)

(58) Field of Classification Search
CPC .. A61F 2/447; A61F 2/44; A61F 2/442; A61F 2/30965; A61F 2310/00407;
(Continued)

(56) References Cited

U.S. PATENT DOCUMENTS

| 2004/0260306 A1* | 12/2004 | Fallin ................. A61B 17/7059 606/104 |
| 2011/0313528 A1* | 12/2011 | Laubert ................. A61F 2/4455 623/17.16 |
| 2013/0297028 A1* | 11/2013 | Zipnick ................. A61F 2/4455 623/17.16 |

FOREIGN PATENT DOCUMENTS

| FR | 2 856 272 A1 | 12/2004 |
| FR | 2856272 | * 12/2004 ............. A61F 2/447 |

(Continued)

OTHER PUBLICATIONS

International Search Report, mailed Oct. 1, 2013 in connection with PCT International Application No. PCT/FR2013/051153, filed May 24, 2013.

*Primary Examiner* — Pedro Philogene
(74) *Attorney, Agent, or Firm* — John P. White; Cooper & Dunham LLP (57) ABSTRACT

A vertebral implant (1) is provided to be implanted in a patient's intersomatic space. The implant (1) includes an intersomatic cage (2) and at least one fixing screw (10) that is intended to be screwed into a bony mass through a well (7) of the cage (2) to stabilize the position of the cage (2) within the intersomatic space. In addition, the well (7) and the screw (10) form a system for the self-locking of the screw (10) in the well (7) in which the screw (10) is locked into position by the well (7).

20 Claims, 4 Drawing Sheets

(52) U.S. Cl.
CPC ....... *A61B 17/8052* (2013.01); *A61F 2/30965* (2013.01); *A61F 2002/30013* (2013.01); *A61F 2002/30014* (2013.01); *A61F 2002/3039* (2013.01); *A61F 2002/30062* (2013.01); *A61F 2002/3079* (2013.01); *A61F 2002/3092* (2013.01); *A61F 2002/3097* (2013.01); *A61F 2002/30266* (2013.01); *A61F 2002/30411* (2013.01); *A61F 2002/30454* (2013.01); *A61F 2002/30492* (2013.01); *A61F 2002/30523* (2013.01); *A61F 2002/30556* (2013.01); *A61F 2002/30579* (2013.01); *A61F 2002/30599* (2013.01); *A61F 2002/30604* (2013.01); *A61F 2002/30616* (2013.01); *A61F 2002/30774* (2013.01); *A61F 2002/30782* (2013.01); *A61F 2002/30904* (2013.01); *A61F 2002/4475* (2013.01); *A61F 2220/0016* (2013.01); *A61F 2310/00407* (2013.01)

(58) Field of Classification Search
CPC .... A61F 2220/0016; A61F 2002/30492; A61F 2002/30523; A61F 2002/30556; A61F 2002/30579; A61F 2002/30604; A61F 2002/30616; A61F 2002/30774; A61F 2002/30782; A61F 2002/3079; A61F 2002/30904; A61F 2002/3092; A61F 2002/3097; A61F 2002/30013; A61F 2002/30; A61B 17/8056

USPC .... 623/17.11–17.16; 606/246–279, 300–308
See application file for complete search history.

(56) References Cited

FOREIGN PATENT DOCUMENTS

| | | |
|---|---|---|
| WO | WO 00/24325 A1 | 5/2000 |
| WO | WO 00/66045 A1 | 11/2000 |
| WO | WO 2009/012195 A1 | 1/2009 |
| WO | WO 2010/019394 A1 | 2/2010 |

* cited by examiner

Fig. 11 ature and may include an orthopaedic plate. This translates into the setting of a cervical plate or a lumbar plate which is installed on the vertebral wall and held by screws implanted in the vertebrae.

Such a solution effectively allows to stabilize the position of the intersomatic cage but has the drawback to add extra-thickness at the vertebral walls and also complicates the setting of the cage by making the surgical intervention more invasive. Indeed, the size of the plate as well as the relative distance between the different screwing positions, located on vertebrae at different stages, involve a rather significant surgical operation.

Any solution implementing little-invasive stabilizing means allowing to hold the cage in position while not preventing the possible removal thereof constitute from then on a major advance in the field of the spinal implants.

VERTEBRAL IMPLANT PROVIDED WITH A SELF-LOCKING AND UNLOCKING MEANS

CROSS-REFERENCE TO RELATED APPLICATIONS

This application is a §371 national stage of PCT International Application No. PCT/FR2013/051153, filed May 24, 2013, claiming priority of French Patent Application No. 1254831, filed May 25, 2012, the contents of each of which are hereby incorporated by reference in their entirety.

TECHNICAL FIELD

The present invention relates to the technical and general field of the fixing systems for the osteosynthesis of the spine and relates in particular to the implants intended to be implanted in the intersomatic space of a patient.

The present invention more particularly relates to a vertebral implant intended to be implanted in the intersomatic space of a patient and comprising an intersomatic cage and at least one fixing screw intended to be screwed into the bony mass through a well of said cage to stabilize the position of said cage within the intersomatic space.

The invention also relates to a vertebral implant intended to be implanted along the intersomatic space of a patient and comprising an intersomatic plate and at least one fixing screw intended to be screwed into the bony mass through a well of said plate to stabilize the position of said plate along the intersomatic space.

These implants have for object to treat various pathologies of the spine such as vertebral compression fractures, scoliosis, lordosis, kyphosis or vertebral instabilities. These pathologies are of course mentioned by way of illustrative and non-limitative example.

These implants are in particular in the form of intersomatic cages. These are hollow implants intended to accommodate a bone-inducing material, such as a bone graft, and are intended to be surgically implanted in the vertebral intersomatic space of a patient, after a suitable preparation, for bone consolidation or fusion of two spinal segments. Such cages may also be used as prostheses to recover a suitable disc height.

The good performance of these cages is based in particular on their position holding over time. Any migration of the cage within the intersomatic space may have particularly harmful consequences for the patient.

If the cage has not been correctly positioned during the surgical intervention, it may create an immediate radicular conflict or be expelled out later as a result of micromovements. There also exist situations where the residual intradiscal pressure may expel the implant. Such situations are from then on synonymous of a dysfunction of the implant and may also require a surgical repairing, which is of course to be banished due in particular to the well-known risks linked to any surgical intervention.

So, to avoid all these problems, any intersomatic cage must also include means for stabilizing its position. Moreover, in cases of great migrations or specific problems linked to the implant, it is sometimes desirable to remove the implant. Hence, these stabilizing means must ideally not prevent the removal of the implant in case of absolute necessity.

PRIOR ART

Conventionally, certain stabilizing means for intersomatic cages are implemented by a posterior pedicular instrumen-

DESCRIPTION OF THE INVENTION

The objects assigned to the present invention consequently aim to remedy the different drawbacks listed hereinabove and to propose a new vertebral implant whose position is stabilized and implementation simplified.

Another object of the invention aims to propose a new vertebral implant easily implantable within the intersomatic space.

Another object of the invention aims to propose a new vertebral implant whose position holding devices are implemented in a little-invasive manner for the patient.

Another object of the invention aims to propose a new vertebral implant whose stabilization means are safe and easy to implement.

Another object of the invention aims to propose a new vertebral implant including stabilizing means and that can be easily removed.

Another object of the invention aims to propose a new vertebral implant that allows an improved osteosynthesis.

The invention finally aims to propose a new medical kit allowing to implant rapidly and efficiently the vertebral implant.

The objects assigned to the invention are achieved by a vertebral implant intended to be implanted in the intersomatic space of a patient and comprising an intersomatic cage and at least one fixing screw intended to be screwed into the bony mass through a well of said cage to stabilize the position of said cage within the intersomatic space, said implant being characterized in that the well and the screw form a system for the self-locking of the screw in the well, said system comprising a male means integral with the screw and a female means formed by the walls of the well, said male and female means being mounted with a relative flexibility allowing, during the screwing of the screw into the bony mass through the well, a progressive and mutual stressing of the male and female means until reaching a final locking position of the screw in which the male and female means are mutually released, the male means being locked in position by the female means, said screw comprising at least a head and a main body, said female means being fixed and said male means being mobile and including a retractable system for modifying the circumference of said head allowing, during the screwing, the relative flexibility between said male and female means.

The objects assigned to the invention are achieved by a vertebral implant intended to be implanted along the intersomatic space of a patient and comprising an intersomatic plate and at least one fixing screw intended to be screwed into the bony mass through a well of said plate to stabilize the position of said plate along the intersomatic space, said implant being characterized in that the well and the screw form a system for the self-locking of the screw in the well, said system comprising a male means integral with the screw and a female means formed by the walls of the well, said male and female means being mounted with a relative flexibility allowing, during the screwing of the screw into the bony mass through the well, a progressive and mutual stressing of the male and female means until reaching a final locking position of the screw in which the male and female means are mutually released, the male means being locked in position by the female means, said screw comprising at least a head and a main body, said female means being fixed and said male means being mobile and including a retractable system for modifying the circumference of said head allowing, during the screwing, the relative flexibility between said male and female means.

The objects assigned to the invention are also achieved thanks to a medical kit formed by a vertebral implant according to the invention and an ancillary for the setting of said vertebral implant in the intersomatic space of a patient.

BRIEF DESCRIPTION OF THE DRAWINGS

Other objects and advantages of the invention will be better understood from the following description, taken in conjunction with the appended drawings, given only by way of illustrative and non-limitative example.

BEST WAY TO IMPLEMENT THE INVENTION

Figures 1, 2, 4:
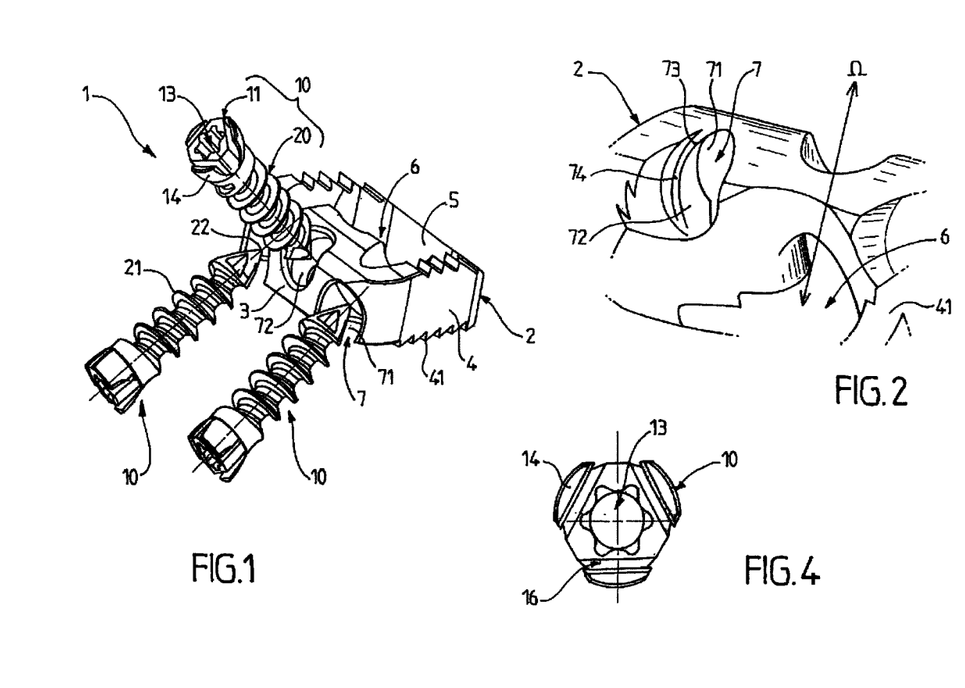
FIG. 1 illustrates in a side perspective view from the front an example of vertebral implant according to the invention, consisted of its different elements.
FIG. 2 shows in a partial side perspective view from the rear an intersomatic cage according to the invention.
FIG. 4 shows an example of a fixing screw viewed from above in a plane perpendicular to the axis of rotation of the screw.

An example of vertebral implant 1 according to the invention is illustrated in FIG. 1. It comprises an intersomatic cage 2 and three fixing screws 10. The number of screws of course corresponds only to one embodiment and may be lower or higher than three. Each screw 10 is consisted of a screw head 11 and a main body 20. The head 11 extends from the apex of the screw 10 to the beginning of a helical thread 21 surrounding the main body 20. A recess 13 is formed in its thickness at the apex of the head 11 of the screw 10. This allows to screw the screw 10 thanks to an object having a reciprocal shape, of the screwdriver type. A Torx recess 13 is shown in the different FIGS. 1, 3, 4 and 6. Of course, any other recess 13 with a different shape (Phillips, hexagonal) may be used. The screw is then extended by the main body 20 consisted of the helical thread 21, which is ended by a tip 22. The thread 21 and the tip 22 are hence particularly adapted for a screwing through the bony mass of a patient. The screws 10 define an axis of rotation $\omega$, which is represented in particular in full line in FIG. 3. The length of the screw 10, from the apex of the head 11 to the tip 22, is for example comprised between 10 and 22 mm.

Advantageously, the cage 2 has a substantially parallelepipedal shape that can be likened to an arch. Hence, it comprises a front face 3, a rear face 5 and two lateral sides 4. The dimensions of the cage 2 will in particular depend on the place where it is supposed to be implanted. Indeed, the implant 1 according to the invention may be intended to be implanted in the intersomatic space, at the cervical or lumbar level.

In the case of a cervical cage 2, the distance between the front 3 and rear 5 faces is comprised between 11 and 16 mm, and the distance between the two lateral sides is comprised between 12 and 20 mm. The height of the cage 2 is directly linked to the pathology of the patient and is comprised between 4.7 and 18 mm. On the other hand, for a lumbar cage, the distance between the front 3 and rear 5 faces of the cage 2 is comprised between 20 and 36 mm, and the distance between the two lateral sides is comprised between 10 and 36 mm. And the height of the cage 2 is comprised between 7 and 18 mm.

Figure 7:
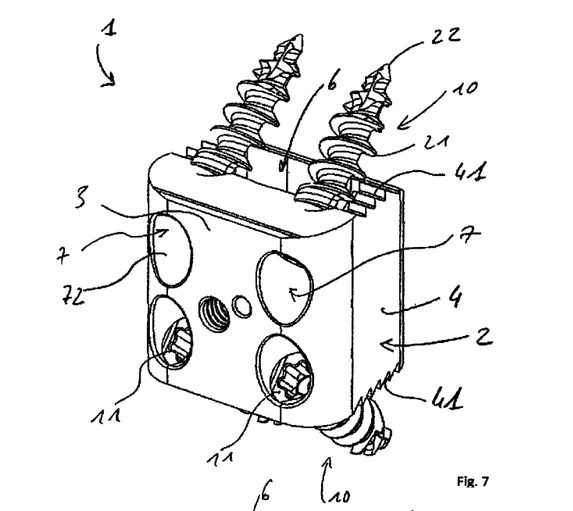
FIG. 7 shows in a perspective view from the front a variant of vertebral implant according to the invention, provided with four fixing screws screwed through the cage.

The height of the cage 2 is chosen as a function the patient's pathology and as a function of the intersomatic space within which the cage 2 is intended to be accommodated. A variant of the invention in which the cage 2 has a height lower than the distance between the front 3 and rear 5 faces is shown in FIG. 1. Another variant of the invention in which the cage 2 has a height substantially equal to or higher than the distance between the front 3 and rear 5 faces is shown in FIG. 7.

The cage 2 also comprises an accommodation 6, at the centre of the parallelepiped, within which a bone-inducing material can be deposited before introducing the cage 2 into the intersomatic space of a patient. This accommodation 6 comprises preferentially no top floor nor bottom floor so that the bone-forming material it is supposed to receive can be in contact with the bony mass of the patient. Hence, the cage 2 is similar to an arch, the front face 3 corresponding to the apex of the arch, the lateral sides 4 to the columns of the arch and the rear face 5 to the floor. The accommodation 6 hence corresponds to the opening of such an arch.

Figure 6:
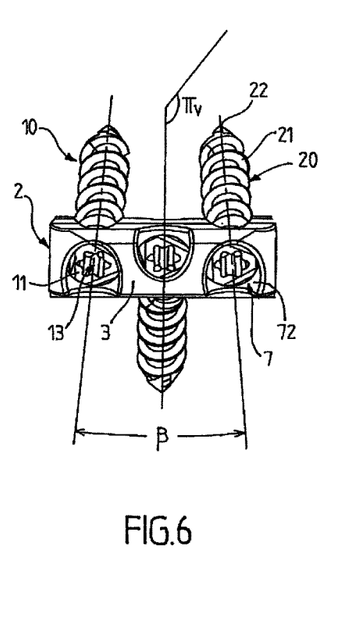
FIG. 6 shows in a front perspective view the vertebral implant according to the invention of FIG. 5, provided with fixing screws screwed through the cage.

It may from then on be easily defined a vertical median plane $\pi_v$ of the cage 2, schematically shown in FIG. 6, which is the plane dividing the cage 2 into a left portion and a right portion of similar horizontal dimensions. It may also be defined a horizontal median plane $\pi_h$ of the cage 2, schematically shown in FIG. 5, which is the plane dividing the cage 2 into an upper portion and a lower portion of similar vertical dimensions.

Figure 8:
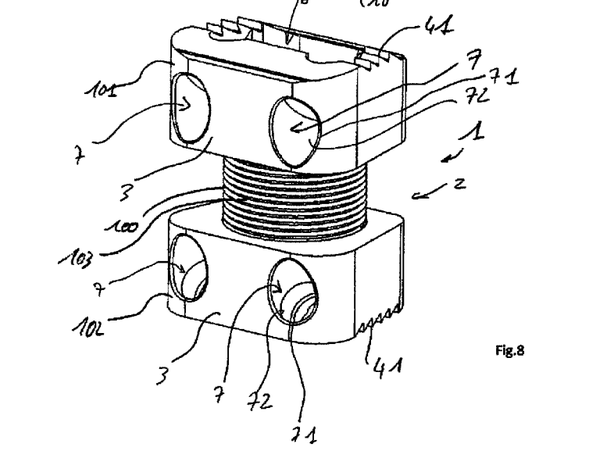
FIG. 8 shows in a perspective view from the front a variant of intersomatic cage provided with a means for adjusting the height of said cage according to the invention.

It is possible to conceive a variant of the invention, shown in FIG. 8, in which the cage 2 is of variable height. For that purpose, the vertebral implant 1 comprises a means 100 for adjusting the height of the cage 2.

Preferably, the adjustment means 100 is an elongation element 103 arranged near the horizontal median plane $\pi_h$ of the cage 2 and separating an upper portion 101 and a lower portion 102 of the cage 2, the activation of the elongation element 103 allowing to move the upper portion 101 away from the lower portion 102 and to hold it at the desired distance from the latter, so as to vary the height of said cage 2.

The elongation element 103 may for example comprise a screw-bolt system, or a rack system. The elongation element 103 allows the cage 2 to take several different sizes so as to be adaptable to several patient's pathological situations.

Figure 9A:
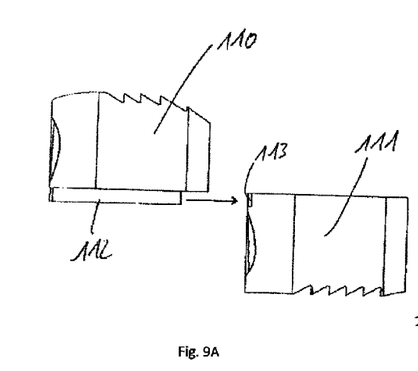
FIG. 9A shows in a side view two separable modules intended to be assembled to form the intersomatic cage according to the invention.
Figure 9B:
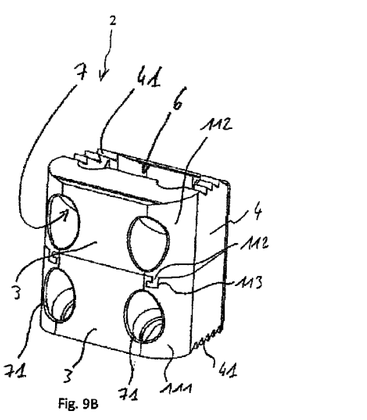
FIG. 9B shows in a perspective view from the front the two modules of FIG. 9A assembled together, forming the intersomatic cage according to the invention.

It is possible to conceive another variant of the invention, shown in FIGS. 9A and 9B, in which the cage 2 is modular, and comprises several separable modules, preferably at least two separable modules, on the one hand an upper module 110 comprising a male connection means 112 and on the other hand a lower module 111 comprising a female connection means 113, said female connection means 113 being designed to cooperate with the male connection means 112 so as to assemble the upper module 110 with the lower module 111 to form said cage 2.

From then on, it is possible to associate, by assembling them, the upper module 110 with the lower module 111, so as to obtain the cage 2 whose properties, such as the shape, the height and/or the number of well 7, will depend on the combined properties of the associated upper 110 and lower 111 modules.

Preferentially, the male connection means 112 comprises a L-shaped slide, the female connection means 113 comprising a L-shaped groove, whose shape is complementary to that of the L-shaped slide, the slide and the groove being designed to slidingly cooperate with each other, so that the assembly of the lower module 111 and the upper module 110 is made by a sliding action.

In order to stabilize the position of the cage 2, the screw(s) 10 must pass through the latter to firmly secure it to the bony mass. Hence, the cage 2 comprises one or more orifices 71 forming wells 7 formed in the thickness of the cage 2.

Figures 3, 5:
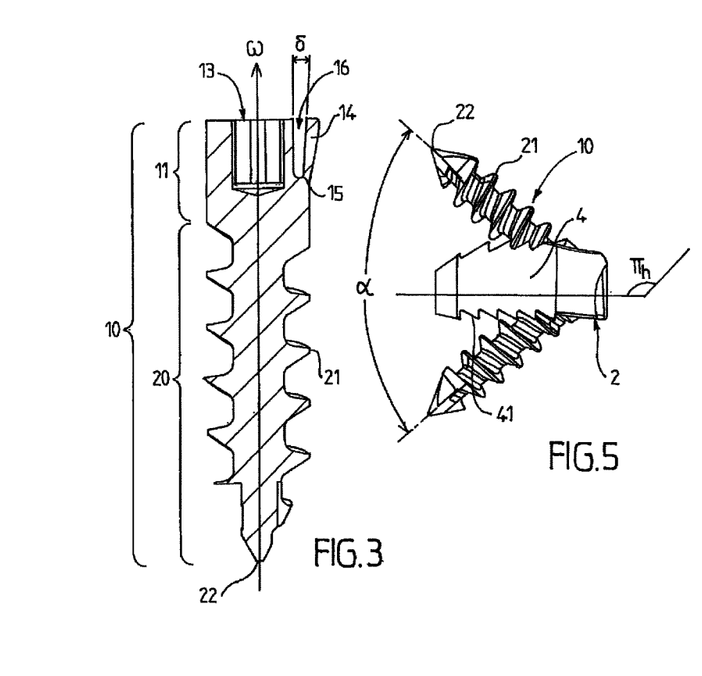
FIG. 3 illustrates in a longitudinal sectional view an example of a fixing screw according to the invention.
FIG. 5 shows in a side view a vertebral implant according to the invention, provided with fixing screws screwed through the cage.

Advantageously, the front face 3 of the face 2, shown for example on the forefront in FIG. 6, is provided with such orifices 71 forming wells 7 in the thickness of the front face 3. Preferentially, the well 7 has an axis of revolution $\Omega$ with symmetrical walls 72 opposite this axis. This axis of revolution $\Omega$ is shown in particular on the central orifice of the cage 2 of FIG. 2. Once the screw 10 positioned in the cage 2 through the well 7, the axis of revolution $\Omega$ of the well 7 and the axis of rotation $\omega$ of the screw 10 are merged with each other. Advantageously, this axis of revolution $\Omega$ forms an angle $\alpha$ comprised between 0 and 45 degrees, more preferentially between 20 and 40 degrees, with the horizontal median plane $\pi_h$ of the cage 2, as illustrated in FIG. 5.

The front face 3 is connected to the rear face 5 thanks to the lateral sides 4 that preferentially comprise retaining teeth 41 formed on the edges thereof. These retaining teeth 41 will allow to help towards the stabilization of the cage within the intersomatic space. These retaining teeth 41 are in particular shown in profile in FIG. 5. They are saw-tooth shaped with an angle comprised between 35 and 50 degrees and a vertical height comprised between 0.5 and 1.6 mm.

Finally, the rear face 5 is consisted of a plate, for example rectangular in shape, which connects the two lateral sides 4 and solidifies the whole structure of the cage.

Besides, the different elements of the vertebral implant 1 according to the invention are made from materials such as titanium, PEEK, PEKK, carbon fibres or a resorbable material.

Advantageously, the cage 2 according to the invention is made from machined titanium and/or from a titanium-based material provided with pores increasing the surface of exchange between the cage and the outside, said pores being obtained by the titanium laser melting technique. This technique allows to create materials including pores able to communicate with each other. The laser accuracy allows to obtain an accurate control of the material macrostructure (porosity size, morphology, distribution). The increase of the surface of exchange between the cage 2 and the patient's tissues allows to substantially improve the osteosynthesis and hence the efficiency of the implant in the treatment of the patient's pathology.

The implant 1 according to the invention comprises at least one fixing screw 10 intended to be screwed into the bony mass through the well 7 of the cage 2, to stabilize the position of the cage 2 within the intersomatic space. This stabilization is hence ensured by the fixing screw 10 that prevent any movement of the implant 1. To ensure the holding in position of the cage 2 over time, it is essential to prevent the unscrewing of the screw 10 that could occur as a result of the micro-movements that the patient may generate during daily displacements or particular movements.

To that end, the well 7 and the screw 10 according to the invention are made so as to form a system for the self-locking of the screw 10 in the well 7, said system comprising a male means integral with the screw 10 and a female means formed by the walls 72 of the wall 7. Said male and female means are mounted with a relative flexibility allowing, during the screwing of the screw 10 into the bony mass through the well 7, a progressive and mutual stressing of the male and female means until reaching a final locking position of the screw 10 in which the male and female means are mutually released, the male means being locked in position by the female means.

Hence, the walls 72 of the well 7 and the male means linked to the fixing screw 10 enter into contact during the screwing of the screw 10 through the well 7 of the cage 2. It results from this contact a stress applied to the male means by the female means, and reciprocally. The respective geometric shapes of the male and female means create a preferably continuous increase of this stress during the progression of the screw 10 in the well 7.

From this stress results a force that will put the male means and/or the female means in movement in a certain respective direction thanks to the flexibility of one or several mobile portions integral with one and/or the other means. This movement continues until the male means reaches the final position where the elasticity of the mobile portion(s) allows the male and/or female means to perform a movement in the opposite direction to come and place in a released position.

The final position is hence a position where the male means is locked by the female means. This locking is made only by screwing of the screw 10 in the well 7 of the cage 2. In this position, the screw 10 is integral with the cage 2, which allows its holding in position over time. This locking hence prevents any migration of the implant.

Preferentially, the male and female means are mounted with a relative flexibility allowing, during the unscrewing of the screw, when the male and female means are in said final position, a mutual stressing of the male and female means until unscrewing the male means from the female means.

Hence, the flexibility between the male and female means that has allowed the self-screwing is sufficient to perform the reverse operation following an unscrewing action. The mobile portions of the male and/or female means are hence elastic enough to allow the screw 10 to exit from the final locking position by a simple unscrewing action. The properties of flexibility as well as the shape of the male and female means are finely chosen so as to allow this to-and-fro movement synonymous of locking and unlocking by screwing and unscrewing operations, respectively.

This unlocking action is hence implemented only by an unscrewing action.

Advantageously, said screw 10 comprises at least a head 11 and a main body 20, said female means is fixed and said male means is mobile and includes a retractable system for modifying the circumference of said head 11 allowing, during the screwing, the relative flexibility between said male and female means.

During the screwing, the walls 72 of the well 7 will hence bear on the retractable system and modify the circumference of the head 11 of the screw 10. This retractable system constitutes from then on a mobile portion of the male means.

Preferentially, the walls 72 of the well 7 form, from the orifice 71 of the well 7 and in the screwing direction, a first area of reduction of the cross-section of the well 7, said first area allowing the radial centripetal compression of said retractable system, up to a shoulder 73 increasing the cross-section of the well and defining a second area allowing the radial centrifugal expansion of said retractable system, said shoulder 73 also forming a circular bearing place 74, perpendicular to the screwing direction, and intended to be in contact with said retractable system when it is in radial expansion. In this embodiment, the female means has no flexible portions. The flexibility is hence ensured only by the retractable means.

The diameter reduction of the well 7 is preferably continuous. The well 7 has hence a conical shape from its orifice 71 to the shoulder 73, as shown in particular in FIG. 2.

The walls 72 of the well 7 will hence apply a force of increasing amplitude on the retractable means. This force will be maximum at the shoulder 73, just before reaching the final position.

The shoulder 73 is the place where the diameter of the well 7 passes in a discontinuous manner from a value of minimum diameter of the shoulder 73 to a value of maximum diameter of the shoulder 73. Hence, the well 7 includes from then on a bearing place 74 forming a crown about the axis of revolution Ω of the well 7. The radial depth of this crown is hence equal to the difference between the maximum diameter and the minimum diameter of the shoulder 73.

This shoulder 73 allows the releasing of the male means, by providing an increase of the circumference of the head 11 of the screw 10. Hence, the retractable means of the head 11 allows it to have a higher diameter than the minimum diameter of the shoulder 73. Advantageously, the upper portion of the retractable means is in contact with the bearing place 74 which allows to perform the locking into position of the screw 10. The difference of value of the stress applied to the retractable means before and after the passage of the shoulder 73 constitutes from then on an energetic barrier that allows to characterize this final position as being a position of equilibrium of the screw 10 within the cage 2. In this situation, the screw 10 cannot be easily dislodged from the cage 2. The holding in position of the cage 2 is then ensured.

On the other hand, during the unscrewing of the screw 10 by a suitable tool, the elasticity of the retractable means can allow the latter to be bent enough to allow the passage of the shoulder 73. This retractable means is hence flexible enough to allow the unlocking thereof by a simple unscrewing action but rigid enough to allow its holding in position when it undergoes only the micro-movements induced by the patient's displacements.

According to the preferential embodiment of the invention, this retractable system may be formed by at least one longitudinal tab 14, connected by its base 15 to said head 11 and hence forming at least one petal extending radially about said head 11, said at least one tab 14 being mounted elastically mobile and having an elastic rest position. FIGS. 1, 3 and 4 allow to clearly illustrate the preferential embodiment of the invention.

FIG. 3 shows in a sectional view a screw 10 whose head 11 is provided with a tab 14 that is connected to the screw 10 only at the base 15 thereof. This connection allows the tab 14 to be able to move in a radial direction (perpendicular to the axis of rotation ω of the screw 10), which has for effect to modify the circumference of the head 11 of the screw 10. This tab 14 is also elastic because it takes a natural elastic rest position when it undergoes no stress.

Advantageously, in the elastic rest position, the longitudinal tab 14 is spaced apart from the axis of rotation ω of the screw 10 by an angle δ comprised between 0 and 25 degrees, preferentially between 0 and 9 degrees, as shown in particular in FIG. 3. Hence, this tab 14 may be angularly spaced apart from the axis of rotation ω of the screw 10 or be substantially parallel to this axis ω. The higher this angle δ, the higher the difference of remoteness from the centre of the screw 10 between the base 15 and the apex of the tab 14. If this tab 14 is substantially parallel to the axis of rotation ω of the screw 10, the remoteness from the centre of the screw 10 will be constant at any point of the tab 14 in the elastic rest position.

The adjustment of the this angle δ of separation between the tab 14 and the axis of rotation ω of the screw 10 allows in particular to adjust the properties of elasticity of the mobile tab 14 to allow it to lock and unlock the screw 10 and the well 7.

There exists, by construction, a hollow space 16 that separates the tab 14 from the head 11 of the screw 10. Hence, when a tab 14 is stressed by the walls of the well, it moves closer to the axis of rotation of the screw 10 thanks to the elasticity of this mobile portion and to the presence of the hollow space 16. The greater this space 16, the greater the potential amplitude of displacement of the screw. Of course, other parameters have an influence on the amplitude of this displacement, as the height, according to the axis of rotation ω of the screw 10, of the tab 14 or the separation angle δ defined hereinabove.

Advantageously, the outer side of the tab 14 is rounded to allow an easy stressing of the screw by the walls 72 of the well 7 during the rotation induced by the screwing.

Preferentially, the tab 14 is made from a material that provides it properties of flexibility so that it can be mobile enough under stress while keeping a certain rigidity to ensure the quality of the locking.

Advantageously, said fixing screw 10 includes three longitudinal tabs 14 arranged about its head 11, as shown in particular in FIGS. 1, 3 and 4.

FIG. 4 shows in particular a screw 10 according to the invention in which three tabs 14 are angularly equidistributed about the head 11 of the screw 10. Each tab 14 extends angularly about the screw 10 by an angle comprised between 60 and 120 degrees. The number of these tabs 14 is adjusted so as to allow a good stability of the screw 10 when it is locked in said final position. A screw 10 including more or less tabs 14 will of course have a similar principle of operation.

The screws 10 are screwed into the patient's bony mass through the cage 2. The screwing directions are determined with the objective to better stabilize the position of the cage 2 within the intersomatic space.

Advantageously, the vertebral implant 1 according to the invention includes several fixing screws 10 and several wells 7, preferably three screws and three wells. Indeed, the number of screws 10 has a direct influence on the holding of the cage 2 within the intersomatic space by increasing the fixing points.

Preferentially, the axis of revolution $\Omega$ of the wells 7 forms an angle $\alpha$ comprised between 0 and 45 degrees, preferentially between 20 and 40 degrees, with the horizontal median plane $\pi_h$ of said cage, as shown in particular in FIG. 5.

It allows to define clearly the angle of penetration of the screw 10 into the patient's bony mass. In this configuration, the screws 10 bear on the bony mass located above and below the implant 1. This multitude of fixing points helps towards the stabilization of the cage 2.

Preferentially, the orifices 71 of the wells 7 are formed on the front face 3 of the cage 2 to allow the practitioner to easily introduce and screw the screws 10 into the patient's bony mass because the position of the orifices is then easily accessible. Said wells 7 are shaped so that the major part of said screws 10 is placed alternately above and below the horizontal median plane $\pi_h$ of said cage 2.

Advantageously, the axis of revolution $\Omega$ of the wells 7 forms an angle $\beta$ with the vertical median plane of said cage comprised between 0 and 20 degrees, as shown in particular in FIG. 6. The screws 10 passing through these wells 7 are oriented in such a manner that the tips 22 are closer to the vertical median plane $\pi_v$ than the heads 11. This allows to ensure that the screws 10 penetrate correctly the bony mass.

According to a variant of the invention illustrated in FIG. 7, the vertebral implant 1 has preferably four fixing screws 10 and four wells 7.

Indeed, increasing the number of screws 10 may allow to increase the holding of the cage 2 within the intersomatic space by increasing the number of fixing points, in particular in the case where the cage 2 has a sufficient size to accommodate four wells 7 and four fixing screws 10.

Preferably, the four fixing screws 10 and the four wells 7 are placed on the cage 2 and oriented symmetrically two-by-two.

An even number of fixing screws 10 allows to symmetrically distribute the fixing points, wherein the fixing screws 10 can be arranged and oriented two-by-two, with for example complementary respective angles of penetration, so as to improve the holding of the cage within the intersomatic space.

By way of variant, the male means being formed by the head 11 of the screw 10, the walls 72 of the wall 7 include mobile portions allowing a modification of the circumference of the well 7, providing during the screwing said relative flexibility between said male and female means. Such a variant is not shown in the different figures.

In such a situation, the screwing of the screw 10 through the well 7 will allow the displacement of the mobile portions of the walls 72 of the well 7. The passage of the screw 10 will then allow the releasing of these mobile walls and hence the locking of the screw 10 within the cage 2. This non-preferential exemplary embodiment will not be detailed but illustrates well all the possible variants of the present invention.

The vertebral implant 1 according to a variant of the invention shown in FIG. 1 is intended to be implanted preferably between two bones of the patient's vertebral column, preferably at the cervical or lumbar level. The shape of the cage 2 is particularly adapted to such an implantation.

The invention also relates to a vertebral implant 1 intended to be implanted along the intersomatic space of a patient and comprising an intersomatic plate 120 and at least one fixing screw 10 intended to be screwed into the bony mass through a well 7 of said plate 120 to stabilize the position of said plate 120 along the intersomatic space, said implant 1 being characterized in that the well 7 and the screw 10 form a system for the self-locking of the screw 10 in the well 7, said system comprising a male means integral with the screw 10 and a female means formed by the walls 72 of the well 7, said male and female means being mounted with a relative flexibility allowing, during the screwing of the screw 10 into the bony mass through the well 7, a progressive and mutual stressing of the male and female means until reaching a final locking position of the screw 10 in which the male and female means are mutually released, the male means being locked in position by the female means, said screw 10 comprising at least a head 11 and a main body 20, said female means being fixed and said male means being mobile and including a retractable system for modifying the circumference of said head 11 allowing, during the screwing, the relative flexibility between said male and female means.

The intersomatic plate 120 is particularly adapted so that the vertebral implant 1 can be implanted in the bony mass of the vertebral column of a patient by lateral way, posterior way or anterior way. The intersomatic plate 120 is for example a cervical plate, or preferably a thoracolumbar plate.

Preferably, the male and female means are mounted with a relative flexibility allowing, during the unscrewing of the screw 10, from said final position, a mutual stressing of the male and female means until unlocking the male means from the female means.

Preferentially, the walls 72 of the well 7 form, from the orifice 71 of the well 7 and in the screwing direction, a first area of reduction of the cross-section of the well 7, said first area allowing the radial centripetal compression of said retractable system, up to a shoulder 73 increasing the cross-section of the well 7 and defining a second area allowing the radial centrifugal expansion of said retractable system, said shoulder 73 also forming a circular bearing place 74, perpendicular to the screwing direction, and intended to be in contact with said retractable system when it is in radial expansion.

Preferentially, the retractable system is formed by at least one longitudinal tab 14, connected by its base 15 to said head 11 and hence forming at least one petal extending radially about said head 11, said at least one tab 14 being mounted elastically mobile and having an elastic rest position.

Preferably, the screw 10 includes three longitudinal tabs 14 arranged about its head 11.

Preferentially, in the elastic rest position, said longitudinal tab 14 is spaced apart from the axis of rotation $\omega$ of the screw 10 by an angle $\delta$ comprised between 0 and 25 degrees, preferentially between 0 and 9 degrees.

Preferentially, the vertebral implant 1 includes several screws 10 an several wells 7, preferably three screws 10 and three wells 7.

Preferably, the screw 10 further comprises at least a head 11 and a main body 20, said male means being formed by said head 11 and the walls 72 of the well 7 including mobile portions allowing a modification of the circumference of the well 7, providing during the screwing said relative flexibility between said male and female means.

Figure 10:
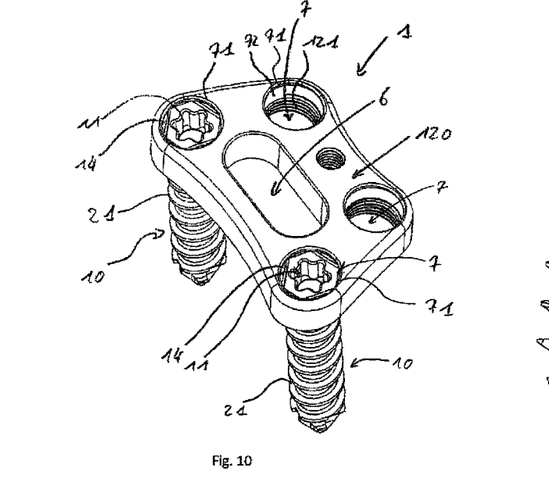
FIG. 10 shows in a perspective view a vertebral implant according to the invention, including an intersomatic plate provided with two fixing screws.
Figure 11:
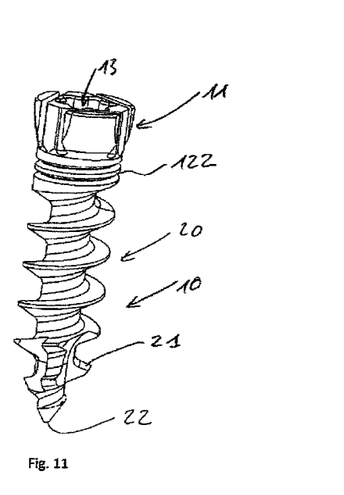
FIG. 11 shows in a perspective view a variant of the screw according to the invention, which includes a head thread.

According to the variant shown in FIGS. 10 and 11, the well 7 includes an inner thread 121 intended to cooperate with a head thread 122 of the screw, said head thread 122 being located at the screw head 11.

When the screw is introduced into the well 7, the interaction of the inner thread 121 with the head thread 122 contributes to the locking of said screw 10 in the well 7.

Hence, a same fixing screw 10 can be associated with either an intersomatic cage 2 or an intersomatic plate 120, so as to form a vertebral implant 1 able to be adapted to the different patient's pathological situations.

Therefore, the invention also relates to a vertebral implant 1 comprising an intersomatic cage 2 intended to be implanted in the intersomatic space of a patient or comprising an intersomatic plate 120 intended to be implanted along the intersomatic space of a patient and at least one fixing screw 10 intended to be screwed in the bony mass through a well 7 of said cage 2 or of said plate 120 to stabilize the position of said cage 2 within the intersomatic space or of said plate 120 along the intersomatic space, said implant 1 being characterized in that the well 7 and the screw 10 form a system for the self-locking of the screw 10 in the well 7, said system comprising a male means integral with the screw 10 and a female means formed by the walls 72 of the well 7, said male and female means being mounted with a relative flexibility allowing, during the screwing of the screw 10 into the bony mass through the well, a progressive and mutual stressing of the male and female means until reaching a final locking position of the screw 10 in which the male and female means are mutually released, the male means being locked in position by the female means, said screw 10 comprising at least a head 10 and a main body 20, said female means being fixed and said male means being mobile and including a retractable system for modifying the circumference of said head 11 allowing, during the screwing, the relative flexibility between said male and female means.

Method of Setting of the Implant 1

The different steps allowing to place a vertebral implant 1 comprising an intersomatic cage 2 and at least one fixing screw 10, in the intersomatic space of a patient, at the cervical or lumbar level, will be described hereinafter.

The vertebral implant 1 is intended to be implanted in the intersomatic space of a patient by anterior or posterior way.

Preferentially, it may be placed in the accommodation 6 of the cage 2 a bone-inducing material, such as a bone graft and/or a substitute, which will allow the bone reconstruction.

To introduce the cage 2 in the intersomatic space of the patient, a specific ancillary is used. Advantageously, said cage 2 includes one or several notches matching the shapes of the ancillary so as to ensure a gripping of the cage. In order for this holding between the ancillary and the cage 2 to be efficient and to prevent in particular any untimely release, the cage 2 includes one or several gripping areas (not shown). They are preferably located on the lateral faces of the cage 2 and are consisted of one or several notches having a shape identical to that of counter-notches present on the adapted ancillary. Preferentially, these notches are asymmetrical on each lateral side 4 of the cage 2 to ensure that the cage 2 is correctly implanted by the practitioner within the intersomatic space by allowing only one gripping direction. This allows to avoid an inverted application of the implant 1 and hence constitute a foolproofing system.

The invention also relates from then on a medical kit formed by a vertebral implant 1 according to the invention and an ancillary for the setting of said vertebral implant 1 in the intersomatic space of a patient.

After having gripped the cage 2 thanks to the specific ancillary, the cage 2 is placed in the patient's intersomatic space. The area of application of the cage 2 has been previously formed by the practitioner to allow this area to receive the implant 1.

Then, at least one fixing screw 10 is screwed through an orifice 71 of said cage into the patient's bony mass, the screwing step ensuring the screwing of the screw 10 into the bony mass then the locking of the screw 10 in the final position within the cage 2.

In the preferential embodiment of the invention, when the head 11 of the screw 10 reaches the well 7 during its screwing, the walls 72 will in particular bear on the longitudinal tabs 14 that are mounted elastically mobile. During the progression of the screw 10, the longitudinal tabs 14 will bend and get closer to the centre of the screw 10 and hence reduce the diameter of the head 11 of the screw 10 until reaching the shoulder 73. At this level, the progression of the screw 10 has for consequence a radial expansion of the tabs 14 and hence an increase of the diameter of the head 11 of the screw 10. The bearing place 74 formed by the shoulder 73 prevents an unscrewing of the screw 10 placed in this final locking position. This hence allows to ensure the stability of the position of the cage 2 within the intersomatic space.

The implant 1 may also be removed from the intersomatic space of a patient if it proves to be necessary. For that purpose, the fixing screw(s) 10 placed in said final position of the patient's bony mass is(are) removed by an unscrewing action, said unscrewing action beginning by the unlocking of the screws 10.

According to the preferential embodiment of the invention, the unscrewing action will create a force on the tabs 14 by bearing in particular on the patient's bony mass through threads 21 of the screw 10. This will generate a sufficient force, higher than the forces usually undergone, on the tabs 14 to use their elasticity and displace them towards the centre of the screw 10 so that the diameter of the head 11 of the screw 10 becomes lower that the minimum diameter of the shoulder 73. Once this shoulder 73 passed, the screw 10 is easily removed by continuing the unscrewing action.

Once all the screws 10 removed, the cage 2 is removed from the intersomatic space of the patient.

Moreover, the intersomatic plate 120 is particularly adapted so that the vertebral implant 1 can be implanted in the bony mass of the vertebral column of a patient by lateral way, posterior way or anterior way.

Hence, the vertebral implant 1 according to the invention proposes a little-invasive solution to ensure the holding in position over time of a cage 2 within the intersomatic space of a patient.

The vertebral implant 1 according to the invention also offers the possibility to be easily removed from the patient's body if it proves to be necessary.

POSSIBILITY OF INDUSTRIAL APPLICATION

The invention finds its industrial application in the design and the manufacturing of vertebral implants and of their system of fixation in the bones of a patient.

The invention claimed is:

1. A vertebral implant (1) intended to be implanted in an intersomatic space of a patient and comprising an intersomatic cage (2) and at least one fixing screw (10) intended to be screwed into the bony mass through a well (7) of said cage (2) to stabilize the position of said cage (2) within the intersomatic space, said implant (1) being characterized in that the well (7) and the screw (10) form a system for the self-locking of the screw (10) in the well (7), said system comprising a male locking portion integral with the screw (10) and a female lock portion formed by the walls (72) of the well (7), said male locking portion and female lock portion being mounted with a relative flexibility allowing, during the screwing of the screw (10) into the bony mass through the well (7), a progressive and mutual stressing of the male locking portion and female lock portion until reaching a final locking position of the screw (10) in which the male locking portion and female lock portion are mutually released, the male locking portion in the final locking position mating with the female lock portion to be locked in position by the female lock portion, said screw (10) comprising at least a head (11) and a main body (20), said female lock portion being fixed and said male locking portion being mobile and including a retractable system for modifying the circumference of said head (11) allowing, during the screwing, the relative flexibility between said male locking portion and female lock portion.

2. The vertebral implant (1) according to claim 1, wherein said male locking portion and female lock portion are mounted with a relative flexibility allowing, during the unscrewing of the screw (10), from said final position, a mutual stressing of the male locking portion and female lock portion until unlocking the male locking portion from the female lock portion.

3. The vertebral implant (1) according to claim 1, wherein the walls (72) of the well (7) form, from an orifice (71) of the well (7) and in the screwing direction, a first area of reduction of the cross-section of the well (7), said first area being configured to allow the radial centripetal compression of said retractable system, up to a shoulder (73) increasing the cross-section of the well (7) and defining a second area allowing the radial centrifugal expansion of said retractable system, said shoulder (73) also forming a circular bearing place (74), perpendicular to the screwing direction, and wherein said shoulder (73) is configured to be in contact with said retractable system when said shoulder (73) is in radial expansion.

4. The vertebral implant (1) according to claim 1, wherein said retractable system is formed by at least one longitudinal tab (14), connected by its base (15) to said head (11) and hence forming at least one petal extending radially about said head (11), said at least one tab (14) being mounted elastically mobile and having an elastic rest position.

5. The vertebral implant (1) according to claim 4, wherein said screw (10) includes three longitudinal tabs (14) arranged about its head (11).

6. The vertebral implant (1) according to claim 4, wherein, in the elastic rest position, the longitudinal tab (14) is spaced apart from an axis of rotation ($\omega$) of the screw (10) by an angle ($\delta$) between 0 and 9 degrees.

7. The vertebral implant (1) according to claim 1, wherein said well (7) has an axis of revolution ($\Omega$) that forms an angle ($\alpha$) between 20 and 40 degrees, with a horizontal median plane ($\pi_h$) of said cage.

8. The vertebral implant (1) according to claim 1, wherein the vertebral implant (1) includes three screws (10) and three wells (7).

9. The vertebral implant (1) according to claim 1, wherein said cage (2) includes at least one notch matching the shapes of a specific ancillary so as to ensure a gripping of the cage.

10. The vertebral implant (1) according to claim 1, wherein said screw (10) comprises a least a head (11) and a main body (20), said male locking portion being formed by said head (11) and the walls (72) of the well (7) including mobile portions allowing a modification of the circumference of the well (7) configured to provide, during the screwing, said relative flexibility between said male locking portion and female lock portion.

11. The vertebral implant (1) according to claim 1, wherein the vertebral implant's (1) elements are made from materials selected from the group consisting of: titanium, polyetheretherketone (PEEK), polyetherketoneketone (PEKK), carbon fibres or a resorbable material.

12. The vertebral implant (1) according to claim 1, wherein said cage (2) is made from a titanium-based material having pores configured to increase the surface of exchange between the cage (2) and the outside of the cage (2), said pores being obtained by the titanium laser melting technique.

13. The vertebral implant (1) according to claim 1, wherein the vertebral implant (1) further comprises a height adjuster (100) for adjusting a height of the cage (2).

14. The vertebral implant (1) according to claim 1, wherein the height adjuster (100) includes an elongation element (103) disposed near a horizontal median plane ($\pi_h$) of the cage (2) and separating an upper portion (101) and a lower portion (102) of the cage, the activation of the elongation element (103) allowing to move the upper portion (101) away from the lower portion (102) and to hold it at a desired distance from the latter, so as to vary the height of said cage (2).

15. The vertebral implant (1) according to claim 1, wherein said cage (2) is modular and comprises a plurality of separable modules.

16. The vertebral implant (1) according to claim 1, wherein said cage (2) comprises at least two separable modules including an upper module (110) comprising a male connector (112) and a lower module (111) comprising a female connector (113), said female connector (113) being designed to cooperate with the male connector (112) so as to assemble the upper module (110) with the lower module (111) to form said cage (2).

17. The vertebral implant (1) according to claim 1, wherein the male connector (112) comprises a L-shaped slide, the female connector (113) comprising a L-shaped groove, whose shape is complementary to that of the L-shaped slide, the slide and the groove being designed to slidingly cooperate with each other, so that the assembly of the lower module (111) and the upper module (110) is made by a sliding action.

18. The vertebral implant (1) according to claim 1, wherein the vertebral implant (1) is implantable between two bones of the patient's vertebral column, at a cervical or lumbar level.

19. A medical kit formed by a vertebral implant (1) according to claim 1 and an ancillary configured to set said vertebral implant in the intersomatic space of a patient.

20. A vertebral implant (1) implantable along an intersomatic space of a patient and comprising an intersomatic plate (120) and at least one fixing screw (10) configured to be screwed into the bony mass through a well (7) of said plate (120) to stabilize the position of said plate (120) along the intersomatic space, wherein the well (7) and the screw (10) of the veterbral implant (1) form a system for the self-locking of the screw (10) in the well (7), said system comprising a male locking portion integral with the screw (10) and a female lock portion formed by the walls (72) of the well (7), said male locking portion and female lock portion being mounted with a relative flexibility allowing, during the screwing of the screw (10) into the bony mass through the well (7), a progressive and mutual stressing of the male locking portion and female lock portion until reaching a final locking position of the screw (10) in which the male locking portion and female lock portion are mutually released, the male locking portion being locked in position by the female lock portion, said screw (10) comprising at least a head (11) and a main body (20), said female lock portion being fixed and said male locking portion being mobile and including a retractable system for modifying the circumference of said head (11) allowing, during the screwing, the relative flexibility between said male locking portion and female lock portion, wherein said male locking portion and female lock portion are mounted with a relative flexibility allowing, during the unscrewing of the screw (10), from said final position, a mutual stressing of the male locking portion and female lock portion until the male locking portion is unscrewed from the female lock portion.

\* \* \* \* \*